(12) United States Patent
Chappuis

(10) Patent No.: US 8,992,616 B2
(45) Date of Patent: Mar. 31, 2015

(54) MODULAR LUMBAR INTERBODY FIXATION SYSTEMS AND METHODS WITH RECONSTRUCTION ENDPLATES

(76) Inventor: James L. Chappuis, Marietta, GA (US)

( * ) Notice: Subject to any disclaimer, the term of this patent is extended or adjusted under 35 U.S.C. 154(b) by 728 days.

(21) Appl. No.: 11/865,872

(22) Filed: Oct. 2, 2007

(65) Prior Publication Data

US 2008/0234826 A1  Sep. 25, 2008

Related U.S. Application Data

(60) Provisional application No. 60/895,595, filed on Mar. 19, 2007.

(51) Int. Cl.
*A61F 2/44* (2006.01)

(52) U.S. Cl.
USPC .................................. 623/17.11; 623/17.16

(58) Field of Classification Search
USPC ..................... 623/17.12, 17.13, 17.15, 17.11
See application file for complete search history.

(56) References Cited

U.S. PATENT DOCUMENTS

| | | | |
|---|---|---|---|
| 5,026,373 A | 6/1991 | Ray et al. | |
| 5,047,030 A | 9/1991 | Draenert | |
| 5,209,450 A | 5/1993 | Grapes | |
| 5,513,838 A | 5/1996 | Van Rossum | |
| 5,728,159 A | 3/1998 | Stroever et al. | |
| 5,753,456 A | 5/1998 | Naqui et al. | |
| 5,871,484 A | 2/1999 | Spievack et al. | |
| 5,971,987 A | 10/1999 | Huxel et al. | |
| 6,019,792 A * | 2/2000 | Cauthen | 623/17.14 |
| 6,045,579 A | 4/2000 | Hochshuler et al. | |
| 6,080,193 A | 6/2000 | Hochshuler et al. | |
| 6,143,033 A | 11/2000 | Paul et al. | |
| 6,231,577 B1 | 5/2001 | Canedy | |
| 6,261,295 B1 | 7/2001 | Nicholson et al. | |
| 6,368,325 B1 | 4/2002 | McKinley et al. | |
| 6,375,681 B1 * | 4/2002 | Truscott | 623/17.11 |
| 6,379,385 B1 | 4/2002 | Kalas et al. | |
| 6,383,221 B1 | 5/2002 | Scarborough et al. | |
| 6,425,920 B1 | 7/2002 | Hamada | |
| 6,517,544 B1 | 2/2003 | Michelson | |
| 6,572,653 B1 * | 6/2003 | Simonson | 623/17.13 |
| 6,576,016 B1 * | 6/2003 | Hochshuler et al. | 623/17.15 |

(Continued)

FOREIGN PATENT DOCUMENTS

| | | |
|---|---|---|
| EP | 0490517 | 6/1992 |
| GB | 2157177 | 10/1985 |
| JP | 751292 | 2/1995 |
| JP | 7222752 | 8/1995 |
| JP | 9149906 | 6/1997 |
| JP | 10211213 | 8/1998 |

OTHER PUBLICATIONS

Brodie, et al., "An Injectable Cementing Screw for Fixation in Osteoporotic Bone," pp. 216-220.

(Continued)

*Primary Examiner* — David Bates
(74) *Attorney, Agent, or Firm* — McHale & Slavin, P.A.

(57) ABSTRACT

Modular lumbar interbody fixation systems and methods with reconstruction endplates are provided. A representative system includes: a pair of engaging plates adapted to fit between and engage the vertebral bodies, at least one engaging plate of the pair of engaging plates being a reconstruction endplate, the reconstruction endplate having a trough and configured to receive a fixing agent; and an alignment device positionable between the pair of engaging plates, the alignment device being operative to maintain a disc space between the vertebral bodies during use.

22 Claims, 2 Drawing Sheets

(56) References Cited

U.S. PATENT DOCUMENTS

| | | | |
|---|---|---|---|
| 7,112,223 B2 * | 9/2006 | Davis | 623/17.16 |
| 7,282,063 B2 * | 10/2007 | Cohen et al. | 623/17.13 |
| 7,309,357 B2 * | 12/2007 | Kim | 623/17.13 |
| 7,351,261 B2 * | 4/2008 | Casey | 623/17.13 |
| 7,458,988 B2 * | 12/2008 | Trieu et al. | 623/17.13 |
| 7,462,196 B2 * | 12/2008 | Fraser et al. | 623/17.11 |
| 2001/0010021 A1 | 7/2001 | Boyd et al. | |
| 2002/0082604 A1 | 6/2002 | Abdelgany et al. | |
| 2002/0120346 A1 | 8/2002 | Boyer, II et al. | |
| 2002/0161449 A1 | 10/2002 | Muschler | |
| 2003/0039676 A1 | 2/2003 | Boyce et al. | |
| 2005/0004572 A1 * | 1/2005 | Biedermann et al. | 606/61 |
| 2007/0050032 A1 * | 3/2007 | Gittings et al. | 623/17.12 |
| 2009/0138083 A1 * | 5/2009 | Biyani | 623/17.11 |

OTHER PUBLICATIONS

Brodie E. McKoy, Yuehuei H. An, "An Injectable Cementing Screw for Fixation in Osteoporotic Bone," pp. 216-220; Orthopaedic Materials Testing Laboratories, Department of Orthopaedic Surgery, Medical University of South Carolina, Charleston, South Carolina.
English Abstract of Japanese Patent Application No. 9149906.
English Abstract of Japanese Patent Application No. 7222752.
English Abstract of Japanese Patent Application No. 10211213.
English Abstract of Japanese Patent Application No. 7051292.

* cited by examiner

MODULAR LUMBAR INTERBODY FIXATION SYSTEMS AND METHODS WITH RECONSTRUCTION ENDPLATES

CROSS-REFERENCE TO RELATED APPLICATION

This application claims priority to U.S. provisional application entitled, "Modular Lumbar Interbody Fixation Systems With Reconstruction Endplates," having Ser. No. 60/895,595, filed on Mar. 19, 2007, which is entirely incorporated herein by reference.

TECHNICAL FIELD

The present invention is generally related to promotion of spinal fusion between neighboring vertebrae.

DESCRIPTION OF THE RELATED ART

The human spine is composed of a column of thirty-three bones, called vertebrae, and their adjoining structures. The twenty-four vertebrae nearest the head are separate bones and are capable of individual movement. These vertebrae are generally connected by anterior and posterior longitudinal ligaments and by discs of fibrocartilage, called intervertebral discs, positioned between opposing faces of adjacent vertebral bodies. The remaining nine vertebrae are fused to form the sacrum and the coccyx and are incapable of individual movement. The vertebral body and the dorsal vertebrae enclose an opening termed the vertebral foramen, through which the spinal cord, a column of nerve tissue which communicates nerve impulses between the brain and the rest of the body, and spinal nerve roots pass and are protected from damage.

Fusion of vertebral bodies may be required for any number of reasons. Most often, such fusion is necessitated when an intervertebral disc is damaged, degenerates, or otherwise becomes diseased, causing great discomfort by way of impinging on the spinal cord and/or nerve roots. When more conservative treatments and minimally invasive procedures have been exhausted, it may become necessary to surgically remove the damaged disk and fuse the associated vertebral bodies in order to restore the original spatial relationships, as well as desired stability.

After an intervertebral disc is removed, an implant device is typically inserted between neighboring vertebrae to maintain normal disc spacing and restore spinal stability, thereby facilitating an intervertebral fusion. An implant device typically contains a pair of engaging elements to engage the vertebrae. Prior to inserting the engaging elements, a vertebral drill is typically inserted within the surgical wound to drill into the cortical endplate and remove fibrous and nuclear material. A vertebral tap may then be used to cut threads into the ends of the neighboring vertebrae. The engaging elements are typically packed with bone graft to facilitate a spinal fusion.

Exemplary devices include those described in U.S. Pat. Nos. 6,045,579 and 6,080,193, which are incorporated herein by reference. These devices incorporate side struts, which are typically formed out of a material such as titanium and are relatively stiff. Because the struts are inflexible, the load distribution may result in accelerated subjacent degeneration of adjacent motion segments.

FIG. 1 schematically depicts adjacent vertebral bodies 102 and 104 that are normal in size and shape. Intervertebral disc 108 fills the space between vertebral bodies 102 and 104. In contrast, FIG. 2 schematically depicts adjacent vertebral bodies 202 and 204 in which upper vertebral body 202 is degraded and intervertebral disc 208 has been removed. In particular, the lower surface of the upper vertebral body is relatively irregularly shaped and, as such, presents a challenge in performing spinal fusion. In this regard, such a vertebral body typically is removed by a corpectomy procedure and an expandable cage or similar device is put in its place. Unfortunately, such procedures are relatively invasive and can place tremendous stress on the patient.

SUMMARY

Modular lumbar interbody fixation systems and methods with reconstruction endplates are provided. An exemplary embodiment of such a system comprises: a pair of engaging plates adapted to fit between and engage the vertebral bodies, at least one engaging plate of the pair of engaging plates being a reconstruction endplate, the reconstruction endplate having a trough and configured to receive a fixing agent; and an alignment device positionable between the pair of engaging plates, the alignment device being operative to maintain a disc space between the vertebral bodies during use.

Another exemplary embodiment of a system comprises: a first pair of engaging plates adapted to fit between and engage a first and a second vertebral body, the first and the second vertebral bodies being adjacent in the spine; a first alignment device positionable between the first pair of engaging plates, the first alignment device being operative to maintain a disc space between the first and the second vertebral bodies during use; a second pair of engaging plates adapted to fit between and engage a third and a fourth vertebral body, the third and the fourth vertebral bodies being adjacent in the spine, the second and the third vertebral bodies being identical or distinct; and a second alignment device positionable between the second pair of engaging plates, the second alignment device being operative to maintain a disc space between the third and the fourth vertebral bodies during use, wherein at least one engaging plate of the first and second pairs of engaging plates is a reconstruction endplate, the reconstruction endplate being configured to receive a fixing agent.

An exemplary embodiment of a method comprises: removing an intervertebral disc between a first and a second vertebral bodies; preparing a first spinal implant comprising: a pair of engaging plates, and an alignment device, wherein at least one engaging plate of the pair of engaging plates is a reconstruction endplate having a trough; filling the at least one reconstruction endplate with a fixing agent; and inserting the first spinal implant between the first and the second vertebral bodies.

Other systems, methods, features and/or advantages will be or may become apparent to one with skill in the art upon examination of the following drawings and detailed description. It is intended that all such additional systems, methods, features and/or advantages be included within this description, be within the scope of the present invention, and be protected by the accompanying claims.

BRIEF DESCRIPTION OF THE DRAWINGS

The invention can be better understood with reference to the following drawings. The components in the drawings are not necessarily to scale, emphasis instead being placed upon clearly illustrating the principles of the present invention. Moreover, in the drawings, like reference numerals designate corresponding parts throughout the several views.

DETAILED DESCRIPTION

Figure 3:
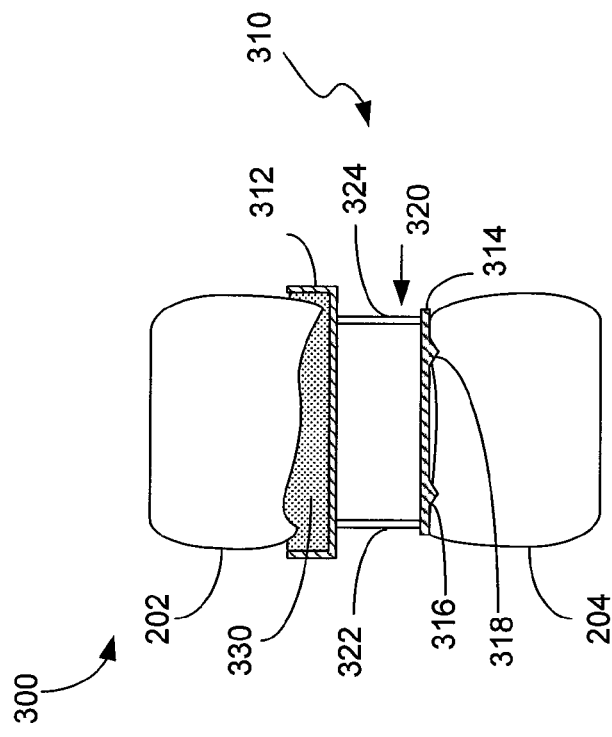
FIG. 3 illustrates a side view of an embodiment of a modular lumbar interbody fixation system with one reconstruction endplate.
Figure 2:
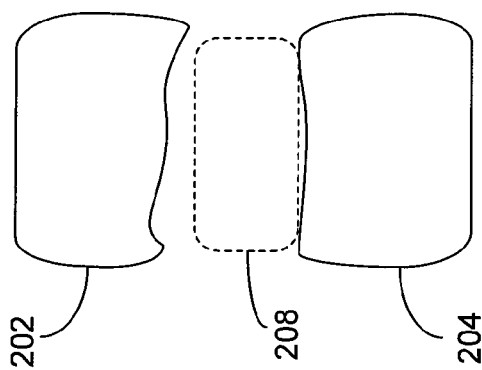
FIG. 2 illustrates a side view of adjacent vertebral bodies in which the upper vertebral body is degraded.
Figure 1:
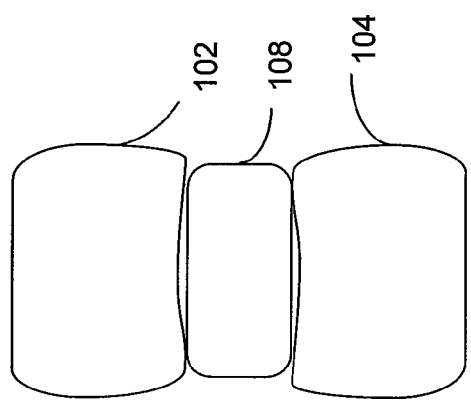
FIG. 1 illustrates a side view of adjacent vertebral bodies that are normal in size and shape.

FIG. 3 illustrates an embodiment of a modular lumbar interbody fixation system 300 with one reconstruction endplate. The modular lumbar interbody fixation system 300 comprises a spinal implant 310 configured to be inserted into the intervertebral space between adjacent vertebral bodies 202 and 204. In this embodiment, the lower surface of vertebral body 202 is degraded and irregularly shaped. Spinal implant 310 comprises engaging plates 312 and 314 and adjustment device 320. Spinal implant 310 is used to replace an intervertebral disc 208 (shown removed in FIG. 2) that has been removed for various reasons including disease, degeneration, etc. Spinal implant 310 is adapted to maintain normal disc spacing, to restore spinal stability, and to facilitate a fusion between vertebral bodies 202 and 204.

Engaging plate 312 is configured to engage with vertebral body 202, and engaging plate 314 is configured to engage with vertebral body 204. Engaging plate 312, in particular, is a reconstruction endplate, which may be shaped like a trough and configured to receive a fixing agent 330, such as cement. When engaging plate 312 is placed in position and filled with fixing agent 330, the fixing agent 330 tends to fill the irregularities of vertebral body 202 and secures engaging plate 312 to vertebral body 202. In other embodiments, engaging plate 314 may also be a reconstruction endplate, to secure engaging plate 314 to a non-degraded vertebral body. Engaging plates 312 and 314 may be constructed of titanium, titanium alloy, ceramics, carbon composites, other metals, etc. Engaging plate 314, which is not specifically a reconstruction endplate in this embodiment, may be securely attached to vertebral body 202 by way of, for example, cement between the respective surfaces, or pins and/or screws inserted through the engaging plate and into the vertebral body it engages. Engaging plate 312 also may be attached by way of, for example, pins and/or screws, to supplement the attachment provided by fixing agent 330. In this regard, in some embodiments, the engaging plates accommodate reconstruction of failed interbody fusion devices and/or total disk replacements. It should also be noted that, in some embodiments, various components, such as wedges, can be used in addition to fixing agent to accommodate deficiencies.

Engaging plates 312 and/or 314 may contain a plurality of openings disposed therein to allow bone development and growth through the engaging plates 312 and 314 and through spinal implant 310. The engaging surfaces of engaging plates 312 and 314 may be substantially planar to provide a relatively large contact area between the engaging plates and vertebral bodies 202 and 204. In this way, subsidence of the vertebral bodies 202 and 204 may be prevented because the force imparted to the vertebral bodies 202 and 204 from the spinal implant 310 is not concentrated across a relatively small area of the vertebral bodies. Alternatively, the engaging surfaces of engaging plates 312 and/or 314 may be nonplanar. The engaging plates may contain a plurality of spikes or protrusions extending toward the vertebral bodies for enhancing an engagement between the vertebral body and the engaging plate. The protrusions may extend into vertebral bodies 202 and/or 204 to prevent spinal implant 310 from moving out of the intervertebral space. In FIG. 3, engaging plate 314 is shown having protrusions 316 and 318 for enhancing an engagement with vertebral body 204.

Adjustment device 320 is configured to fit between engaging plates 312 and 314. Adjustment device 320 comprises two struts, 322 and 324, but adjustment device 120 may comprise one or more struts in other embodiments. As described herein, a "strut" refers to any support member disposed between engaging plates 312 and 314 to separate engaging plates 312 and 314. Struts 322 and 324 may be attached to engaging plates 312 and 314 and/or attached directly to vertebral bodies 202 and 204. Notably, struts may be relatively stiff struts or relatively flexible. In some embodiments, varying degrees of flexibility can be provided which can provide better load distribution for preventing accelerated subjacent degeneration of adjacent motion segments.

Struts 322 and 324 may have a predetermined height that defines the height of the spinal implant 310. By way of example, a strut can have a nominal height of between approximately 30 mm and approximately 40 mm. Alternatively, struts 322 and 324 may each have an adjustable height. Engaging plates 312 and 314 may be configured to receive struts of various heights to allow the height of spinal implant 310 to be varied to fit the needs of the patient. In an embodiment, the struts 322 and 324 have differing heights to cause the height of spinal implant 310 to vary. In this manner, spinal implant 310 may be used to correct a lateral deviation in the spinal column as may occur in scoliosis. Struts 322 and 324 may contain a hinge pin to allow an upper member of the strut to pivot with respect to a lower member of the strut. In this manner, the struts may be pivoted such that the ends of the struts are properly aligned when a height difference exists between struts 322 and 324.

Spinal implant 310 may contain a retaining plate proximate the posterior end to provide a backing against which bone graft may be packed and to maintain bone graft between the engaging plates. The retaining plate may be substantially planar and may contain openings to allow bone ingrowth therethrough. A removable endcap may be positioned proximate the anterior end to contain bone graft within the fusion device and to prevent the migration of bone graft outside the engaging plates. The endcap may contain one or more openings for allowing bone ingrowth between a vertebral body and bone graft contained between the engaging plates. The endcap may be made of a plastic material, such as polyethylene, that tends to be non-irritating and non-abrasive to the surrounding tissues.

Figure 4:
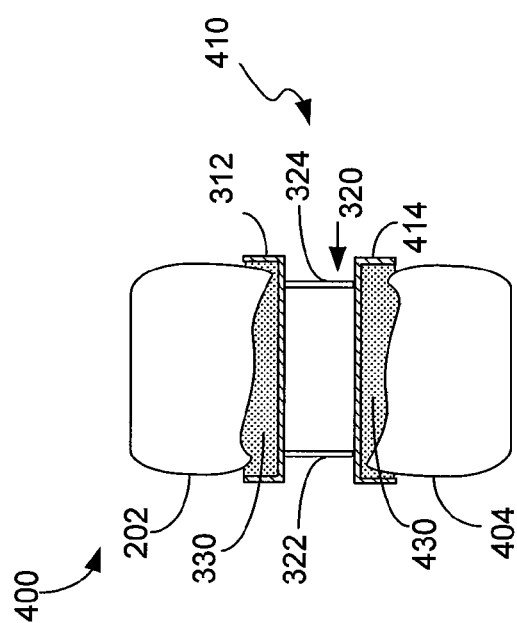
FIG. 4 illustrates a side view of an embodiment of a modular lumbar interbody fixation system with two reconstruction endplates.

FIG. 4 illustrates an embodiment of a modular lumbar interbody fixation system 400 with two reconstruction endplates. In this embodiment, vertebral bodies 202 and 404 both are degraded, having irregularly shaped surfaces facing the intervertebral space where an intervertebral disc has been removed. In spinal implant 410, which is configured to fit in the intervertebral space between vertebral bodies 202 and 404, engaging plates 312 and 414 are both reconstruction endplates. As a reconstruction endplate, engaging endplate 414 may be shaped like a trough and configured to receive a fixing agent 430, such as cement. When engaging plate 414 is placed in position and filled with fixing agent 430, the fixing agent 430 tends to fill the irregularities of vertebral body 404 and secures engaging plate 414 to vertebral body 404.

Figure 5:
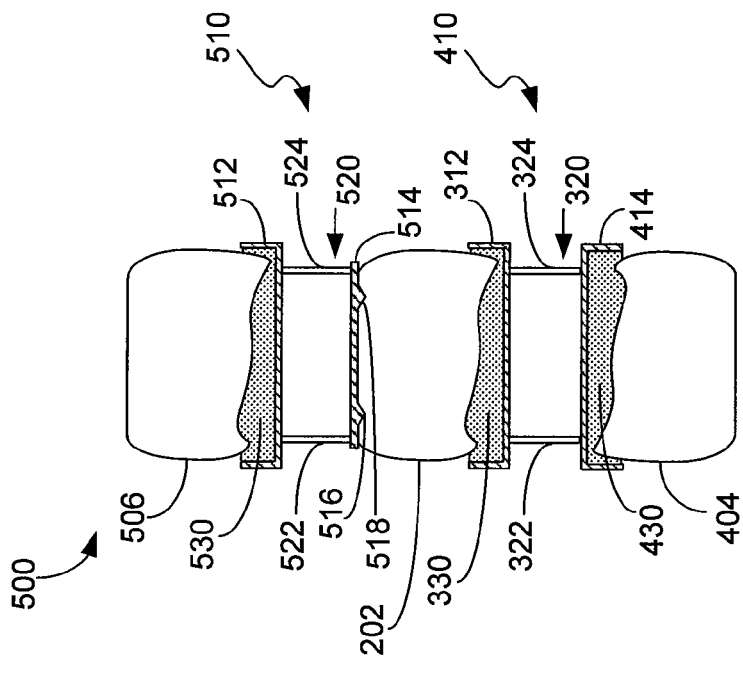
FIG. 5 illustrates a side view of another embodiment of a modular lumbar interbody fixation system with multiple reconstruction endplates.

FIG. 5 illustrates an embodiment of a modular lumbar interbody fixation system 500 with multiple reconstruction endplates. In modular lumbar interbody fixation system 500, three adjacent vertebral bodies are depicted, vertebral bodies 506, 202, and 404. Here, vertebral body 506 also is degraded, having at least an irregular lower surface. However, in other embodiments, vertebral body 506 may not be degraded. Spinal implant 410, described above in connection with FIG. 4, is inserted in the intervertebral space between vertebral bodies 202 and 404. Additionally, spinal implant 510 is inserted in the intervertebral space between vertebral bodies 506 and 202. In other embodiments, spinal implant 510 may be inserted between vertebral bodies above or below vertebral bodies 506 and 202 and need not be adjacent to or inclusive of vertebral bodies 506 and 202.

Spinal implant 510 is similar to spinal implant 310, described above in connection with FIG. 3, in that spinal implant 510 comprises engaging plates 512 and 514 and adjustment device 520. Engaging plates 512 and 514 are similar to engaging plates 312 and 314. In particular, engaging plate 512 is a reconstruction endplate, configured to receive cement 530. Additionally, engaging plate 514 may be a reconstruction endplate also in other embodiments. As depicted, engaging plate 514 has protrusions 516 and 518 to better engage with vertebral body 202, but these protrusions are optional, and there may be one protrusion or more than two protrusions if desired. Adjustment device 520, similar to adjustment device 320, comprises two struts, 522 and 524, but adjustment device 520 may comprise one or more struts in other embodiments. Struts 522 and 524 may be similar to struts 522 and 524, but may differ in stiffness. In particular, depending on the needs of the patient, struts 522 and 524 may be relatively more stiff than struts 522 and 524, or struts 522 and 524 may be relatively more flexible than struts 322 and 324.

In other embodiments, three or more spinal implant devices may be used, with or without reconstruction endplates as desired, with the struts of each spinal implant device having varying degrees of flexibility. Clearly, in some applications, gradation from stiffer to more flexible devices can occur in both directions along the spine.

It should be emphasized that the above-described embodiments are merely possible examples of implementations. Many variations and modifications may be made to the above-described embodiments without departing substantially from the spirit and principles of the invention. All such modifications and variations are intended to be included herein within the scope of this disclosure and the present invention and protected by the following claims.

Therefore, having thus described the invention, at least the following is claimed:

1. A method for promoting fusion between adjacent vertebral bodies comprising the steps of:
providing a modular lumbar interbody fixation device comprising a pair of engaging plates adapted to fit between and engage the vertebral bodies, at least one engaging plate of the pair of engaging plates being a reconstruction endplate, the reconstruction end plate having a trough defined by a closed and flat bottom and a sidewall having a continuous upper surface and extending continuously about a periphery of the flat bottom whereby an inner diameter of said side wall is sized to receive and support an outer diameter of a vertebral body therein, said sidewall extending away from said substantially closed and flat bottom by a distance, said distance between said continuous upper surface and said closed and flat bottom being substantially constant about said periphery, the trough being sized and shaped to receive therein a fixing agent and an entire end of said vertebral body such that engagement of the fixing agent with the end of the vertebral body affixes the end of the vertebral body within the trough; and an alignment device comprising at least two independent struts positionable between the pair of engaging plates, the alignment device being operative to maintain a disc space between the vertebral bodies during use;
filling at least one of said engaging plates with a fixing agent; and
inserting said modular lumbar interbody fixation device between a first and a second vertebral body.

2. The method of claim 1, wherein the reconstruction endplate is operative to engage an irregular surface of a vertebral body.

3. The method of claim 1, wherein the fixing agent is cement.

4. The method of claim 1, wherein both engaging plates are reconstruction end plates.

5. The method of claim 1, wherein the reconstruction endplate further comprises protrusions extending from within the trough for enhancing an engagement between the vertebral body and the engaging plate, the protrusions being adapted to extend into the vertebral body.

6. The method of claim 1 wherein said at least two independent struts of the alignment device are fixedly attached to said pair of engaging plates.

7. The method of claim 1 wherein each of said at least two independent struts of the alignment device are of different height.

8. The method of claim 1 wherein each of said at least two independent struts of the alignment device have adjustable heights.

9. The method of claim 1 wherein the at least two independent struts of the alignment device are flexible.

10. The method of claim 1 wherein said engaging plates include a wedge shaped surface.

11. The method of claim 1 wherein at least one end plate contains openings sized to allow bone ingrowth therethrough while maintaining said vertebral body in a position above said end plate.

12. A method for promoting fusion between adjacent vertebral bodies comprising the steps of:
providing a first modular lumbar interbody fixation device comprising a first pair of engaging plates adapted to fit between and engage a first and a second vertebral body, the first and the second vertebral bodies being adjacent in the spine;
said first modular lumbar interbody fixation device further comprising a first alignment device having at least two independent first struts positional between the first pair of engaging plates, the first alignment device being operative to maintain a disc space between the first and the second vertebral bodies during use;
providing a second modular lumbar interbody fixation device comprising a second pair of engaging plates adapted to fit between and engage a third and a fourth vertebral body, the third and the fourth vertebral bodies being adjacent in the spine, the second and the third vertebral bodies being identical or distinct; and
said second modular lumbar interbody fixation device further comprising a second alignment device having at least two independent second struts positionable between the second pair of engaging plates, the second alignment device being operative to maintain a disc space between the third and the fourth vertebral bodies during use,
wherein at least one engaging plate of the first and second pairs of engaging plates is a reconstruction endplate, the reconstruction endplate having a trough defined by a closed and flat bottom and a sidewall having a continuous upper surface and extending continuously about a periphery of the closed and flat bottom, said sidewall extending away from said closed and flat bottom by a distance whereby said side wall having an inner diameter sized to receive and support an outer diameter of a vertebral body therein, said distance between said continuous upper surface and said closed and flat bottom being substantially constant about said periphery, the trough being sized and shaped to receive therein a fixing agent and an entire end of said-vertebral body such that engagement of a fixing agent with the end of said vertebral body affixes the entire end within the trough;
filling at least one engaging plate of said first pair of engaging plates of said first modular lumbar interbody fixation device with a fixing agent;
filling at least one engaging plate of said second pair of engaging plates of said second modular lumbar interbody fixation device with a fixing agent;
inserting said first modular lumbar interbody fixation device between said first and said second vertebral body; and
inserting said second modular lumbar interbody fixation device between said third and said fourth vertebral body.

13. The method of claim 12, wherein the fixing agent is cement.

14. The method of claim 12, wherein the at least two struts of the second alignment device are relatively more flexible than the at least two struts of the first alignment device.

15. The method of claim 12 wherein said first alignment device is fixedly attached to said first pair of engaging plates and said second alignment device is fixedly attached to said second pair of engaging plates.

16. The method of claim 12 wherein each of said first and second alignment devices are of different heights.

17. The method of claim 12 wherein each of said first and second alignment devices have adjustable heights.

18. The method of claim 12 further including the steps of:
providing at least one additional
modular lumbar interbody fixation device comprising a pair of engaging plates adapted to fit between and engage at least two additional vertebral bodies, at least one engaging plate of the pair of engaging plates being a reconstruction endplate, the reconstruction end plate having a trough defined by a closed and flat bottom and a sidewall having a continuous upper surface and extending continuously about a periphery of the flat bottom whereby an inner diameter of said side wall is sized to receive and support an outer diameter of a vertebral body therein, said sidewall extending away from said substantially closed and flat bottom by a distance, said distance between said continuous upper surface and said closed and flat bottom being substantially constant about said periphery, the trough being sized and shaped to receive therein a fixing agent and an entire end of said at least one additional vertebral body such that engagement of the fixing agent with the end of the vertebral body affixes the end of the vertebral body within the trough; and an alignment device comprising at least two independent struts positionable between the pair of engaging plates, the alignment device being operative to maintain a disc space between the at least two additional vertebral bodies during use; and
filling at least one engaging plate of said at least one additional modular lumbar interbody fixation device with a fixing agent;
inserting said at least one additional modular lumbar interbody fixation device between said at least two additional vertebral bodies.

19. The method claim 12 wherein each of said independent struts are flexible.

20. The method claim 12 wherein each said pair of independent struts have different degrees of flexibility.

21. The method of claim 18 wherein each said pair of independent struts have varying degrees of flexibility along at least one direction of the spine.

22. The method of claim 12 wherein at least one end plate contains openings sized to allow bone ingrowth therethrough while maintaining said vertebral body in a position above said end plate.

* * * * *